United States Patent [19]

Nomura

[11] Patent Number: 5,750,107
[45] Date of Patent: May 12, 1998

[54] HAIR GROWTH PROMOTER

[76] Inventor: Manabu Nomura, 2763-7, Ohaza Imaizumi Kiyotake-cho, Miyazaki-gun Miyazaki 889-16, Japan

[21] Appl. No.: 661,970

[22] Filed: Jun. 12, 1996

Related U.S. Application Data

[63] Continuation-in-part of Ser. No. 167,828, filed as PCT/JP93/00187, Feb. 12, 1993, abandoned.

[51] Int. Cl.$^6$ ................................................ A61K 35/78
[52] U.S. Cl. ................................................ 424/195.1
[58] Field of Search ................................ 424/195.1

[56] References Cited

U.S. PATENT DOCUMENTS

| | | | |
|---|---|---|---|
| 4,515,778 | 5/1985 | Kastell | 424/569 |
| 5,108,749 | 4/1992 | Hua | 424/195.1 |

FOREIGN PATENT DOCUMENTS

| | | |
|---|---|---|
| 57-102809 A | 6/1982 | Japan. |
| 1038012 | 2/1989 | Japan. |
| 2-279618 | 11/1990 | Japan. |
| 5155738 | 6/1993 | Japan. |

OTHER PUBLICATIONS

Ogawa et al., Current Problems In Dermatology 11: 159–170 (1983).

Bazzano et al., *J. Inv. Dermatol.*, 101 (1)(Supp.):138S–142S, Jul. 1993.

Brenner et al., *Harefriah*, 121 (9):297–302, Nov. 1991.

Dawber, in *The Science of Hair Care*, Ch. 17, 451–467, Charles Zviak, ed., Marcel Dekker, New York, 1986.

Gonzales et al., in *Conn's Current Therapy*, pp. 599–603, Robert E. Rakel, ed., W.B. Saunders Co., Philadelphia, 1984.

Hattori et al., *J. Dermatol.*, 10:45–54, 1983.

Houssay et al., *Acta physiol. latinoam.*, 26:186–91, 1976.

Ibrahim et al., *J. Embryol. ex. Morph.*, 33(4):831–44, 1975.

Kobayashi et al., *Yakugaku Zasshi*, 113(10):718–24, Oct. 1993 (Abstr.).

Mellin et al., *J. Steroid Biochem. Mol. Biol.*, 44(2):121–31, Feb. 1993.

Ogawa et al., *J. Dermatol.*, 13:126–31, 1986.

Ogawa et al., *Curr. Prob. Dermatol.* (Switzerland), 11:159–170, 1983.

Olsen et al., *J. Am. Acad. Dermatol.* 23(3 Pt. 1):470–72, Sep. 1990.

Redmond et al., *Cleve. Clin. J. Med.*, 57(5):428–32, Jul.–Aug. 1990.

Rushton et al., *Clin. Exp. Dermatol.*, 14(1):40–46, Jan. 1989.

Sundberg et al., *J. Inv. Dermatol.*, 104(5):16S–17S, May 1995.

Sundberg et al., *J. Inv. Dermatol.*, 104(5):32S–33S, May 1995.

*The Merck Manual of Diagnosis and Therapy*, Ch. 238, 2433–2434, Merck Res. Lab., N.J., 1992.

Trachy et al., *Ann. N.Y. Acad. Sci.* (U.S.), 642:468–69, 1991.

*Primary Examiner*—Jean C. Witz
*Attorney, Agent, or Firm*—Sheridan Ross P.C.

[57] ABSTRACT

The present invention relates to a composition useful in as a hair growth promoter which contains an extract drawn from a plant having a pseudo bulb selected from the group consisting of Calanthe R. Br. and Phaius Lour. The extract can be obtained from either a portion of a plant or the pseudo bulb of *Calanthe discolor* Lindl. or *Phaius flavus* (Blume) Lindl. by extraction of such a plant in an extraction solvent. The composition may include vitamins, amino acids, animal and plant oils, and sodium chloride. When applied to an area of skin afflicted with alopecia, the composition is useful for promoting hair growth.

25 Claims, 3 Drawing Sheets

| Date | 2% Calanthe Extract | 4% Calanthe Extract |
|---|---|---|
| 18 Days | 20.429 ± 4.992% | 25.550 ± 21.292% |
| 24 Days | 42.716 ± 16.780% | 32.571 ± 26.063% |
| 30 Days | 52.661 ± 15.900% | 44.586 ± 27.701% |
| 37 Days | 65.071 ± 21.023% | 59.426 ± 11.328% |
| 43 Days | 74.836 ± 22.383% | 71.257 ± 11.188% |

*Fig. 3*

HAIR GROWTH PROMOTER

CROSS REFERENCE TO RELATED APPLICATIONS

The present application is a continuation-in-part of U.S. Ser. No. 08/167,828 filed Dec. 16, 1993, now abandoned, which is a United States national phase application based on PCT/JP93/00187, Feb. 12, 1993 which has a priority date of Feb. 17, 1992. These applications are incorporated by reference herein in their entirety.

FIELD OF THE INVENTION

The present invention relates to a hair growth promoter useful in the treatment of alopecia, and a method of producing such a promoter.

BACKGROUND OF THE INVENTION

Alopecia, or the unnatural absence of hair (i.e., baldness), is a common affliction among humans and can be caused by a variety of conditions. Androgenic alopecia, also known as male pattern baldness, is associated with elevated levels of 5 alpha-reductase, which converts testosterone to dihydrotestosterone which adversely affects the hair follicles. *Alopecia areata*, which can result in patchy loss of hair, *alopecia totalis* (complete loss of scalp hair), or *alopecia universalis* (complete loss of body hair), have been proposed to be caused by an autoimmune disease because of the infiltration of the hair follicles with lymphocytes. Alopecia can also be caused by trauma such as stress, hair-pulling, and illness. Although various treatments, such as topical compositions, have been used to alleviate hair loss and promote the growth of new hair in patients with alopecia, these prior compositions suffer from problems which include lack of effectiveness, patchy hair regrowth, slow progress, and irritation of the skin. Therefore, there remains a need for an effective and safe hair growth promoter. Furthermore, since different types of alopecia are caused by different physiological mechanisms, there is a need for safe hair growth promoters which may be used in conjunction with other medications and treatments for alopecia in order to enhance the effects of such treatments on hair growth.

The C3H mouse strain has been widely used as an animal model for investigating hair growth mechanisms and for determining the effectiveness of promoters or inhibitors of hair growth (see, for example, Ogawa et al., pp 159–170, 1983, *Curr. Probl. Dermatol. Swit.*, vol. 11; Bazzano et al., pp 138S–142S, 1993, *J. Invest. Dermatol.*, vol 101; Trachy et al., pp 468–469, 1991, *Ann. N. Y. Acad. Sci. U.S.*, vol 642; Kobayshi et al., pp.718–724, 1993, Yakugaky Zasshi, vol. 113; and Ibrahim et al., pp 831–844, 1975, *J. Embryol. Exp. Morphol.*, vol. 33). Unlike human hair follicles, which are asynchronous in resting (telogen) and growing (anagen) phases, C3H mouse hair follicles are synchronized with respect to growth pattern, which has been well documented with respect to the life cycle of the mouse. Thus, it is possible to determine when all of the hair follicles of a C3H mouse are in a resting or a growing phase by knowing the age of the mouse. Since the growth phase of all of the hair follicles can be simultaneously determined and evaluated, experiments can be designed to manipulate the growth phase and to determine the effects of various treatments and compositions on hair growth. Therefore, use of the C3H mouse model of hair growth is a widely accepted means of demonstrating the pharmacological effectiveness of a hair growth promoter.

Conventionally, a variety of hair growth promoters have been used to prevent and treat the physiological symptoms of various types of alopecia which may result in balding and thinning of the hair. Such hair growth promoters have been proposed to facilitate circulation of the blood, activate the hair matrix cells, inhibit the secretion of lipids from the scalp skin, and supplement nutrition to the hair.

Prior investigators have prepared compositions for use in the promotion of hair growth by using active ingredients such as glyceride pentadecanate, cepharanthin, Swertia extract liquid, soluble cysteine, ginseng extract liquid, e-menthol, isopropylmethylphenol, glycyrrhetinic acid, tocopherol acetate, hinokitiol, capsicum tincture, sweet grass extract, nicotinamide, salicylic acid. These substances have been proposed to promote hair growth.

Some hair growth promoters in the prior art include an active ingredient extracted from plants. For example, prior investigators have proposed using extracts from the Orchidaceae species, *Bletilla striata*, and from plants of the Meliaceae and Lamiaceae families in hair growth promoters (Japanese patent JP 1038012 (abstract), Japanese patent JP 5155738 (abstract); and Kobayashi, et al., pp.718–724, 1993, Yakugaky Zasshi, vol. 113).

Although some of these proposed hair growth promoters may temporarily control severe loss of hair, thinning of the hair is often not controlled. Moreover, the loss of hair recurs over time or upon cessation of the treatment. Furthermore, the use of conventional medications and remedies in a patient whose hair has been lost entirely may only produce downy hair during the first six months after application of the promoter, and often no further hair growth can be expected. Some products may also have an adverse reaction with the scalp such as dandruff, itching, rashes, or other irritation, which occurs with extended use of the product. Due to the lack of success of prior hair growth promoters, therefore, there remains a need for ingredients which promote activation of the hair root, facilitate the growth and strengthening of the hair, and are safe to use on the skin. As such, there remains a need to develop a safe and effective hair growth promoter.

SUMMARY OF THE INVENTION

The present invention is directed, in one embodiment, to a composition which is useful for promoting hair growth when applied to an area of skin that is afflicted with alopecia. The composition of the present invention comprises an extract of a plant having a pseudo bulb, wherein the plant is of a genera selected from Calanthe R. Br. and Phaius Lour. In a preferred embodiment, the extract is derived from the entire plant. In another preferred embodiment, the extract is derived from the pseudo bulb of such a plant. In another preferred embodiment, the plant is selected from the group *Calanthe discolor* Lindl. and *Phaius flavus* (Blume) Lindl.

In another embodiment, the composition of the present invention further comprises at least one component selected from the group consisting of vitamins, amino acids, animal oils, plant oils, sodium chloride, and mixtures thereof. Preferred components of the composition of the present invention include biotin H, sesame oil, sodium chloride, 2-amino-3-(3,4-dihydroxyphenyl)propanoic acid, germ oil, sodium pantothenate, potassium pantothenate, niacin, and animal oil.

Another embodiment of the present invention is a process for producing an extract from a plant of a genera selected from Calanthe R. Br. and Phaius Lour. that is used as an active ingredient in a composition useful for promoting hair growth. This process includes contacting a portion of such a plant with an extraction solvent.

Another embodiment of the present invention is a method to promote the growth of hair on a portion of skin that is afflicted with alopecia. Such a method includes applying a composition comprising an extract of a plant of a genera selected from Calanthe R. Br. and Phaius Lour. to a portion of the skin affected with alopecia. In preferred embodiments, such a method includes a composition further comprising a component selected from the group consisting of vitamins, amino acids, animal oils, plant oils and sodium chloride.

Another embodiment of the present invention relates to a composition useful as a hair growth promoter which has at least one active ingredient which is present in an extract of a plant of a genera selected from Calanthe R. Br. and Phaius Lour.

BRIEF DESCRIPTION OF THE FIGURES

FIG. 3 shows percentages of hair regrowth in shaved C3H mice that have been treated with an extract derived from *Calanthe discolor* Lindl.

DETAILED DESCRIPTION OF THE INVENTION

Figure 1:
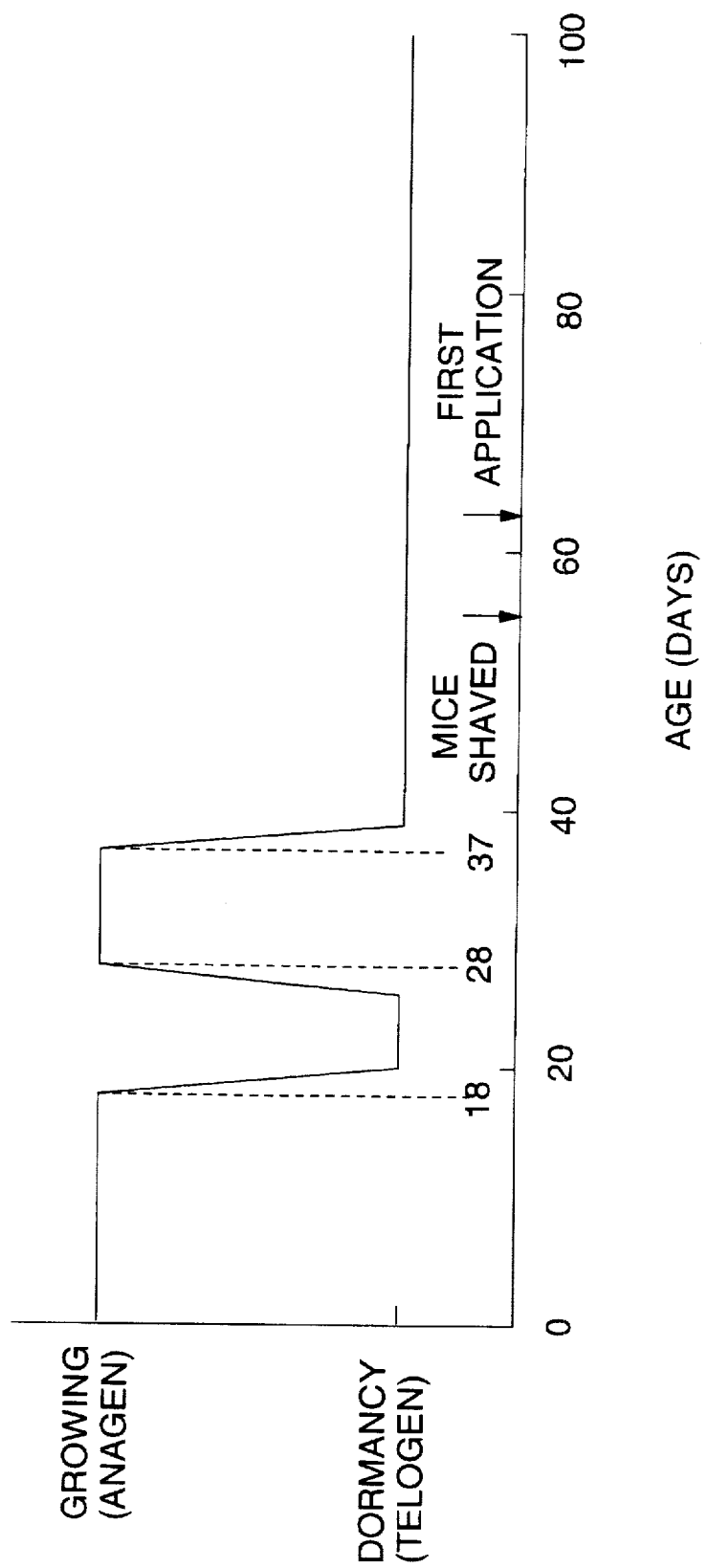
FIG. 1 illustrates the hair growth cycle in C3H mice.

The present invention relates to a composition which is useful in promoting hair growth when applied to an area of skin that is afflicted with alopecia. The hair growth promoter composition of the present invention comprises a plant extract drawn from plants of the family Orchidaceae which have a pseudo bulb and belong to the genera Calanthe R. Br., and Phaius Lour. Among these genera, extracts of *Calanthe discolor* Lindl., and *Phaius flavus* (Blume) Lindl. are preferred.

The active ingredients useful for promoting hair growth in the composition of the present invention are present in an extract drawn from portions including, but not limited to the flower, root, stem, leaf, or entire body of the above-mentioned Orchidaceae plants which have a pseudo bulb. As used herein, "a portion of a plant" can refer to any of the above mentioned portions, including the whole, or entire, plant. In one embodiment of the present invention, the extract is drawn from the whole plant. In another preferred embodiment of the present invention, the extract is drawn from a pseudo bulb of the plant since it exhibits superior hair growth properties. As used herein, a pseudo bulb refers to a portion of an Orchidaceae plant of the present invention that has a bulb-like appearance and stores water and nutrients for the plant. A pseudo bulb can also be referred to as a subterranean stem or a rhizome, when the bulb is located under ground.

It is within the scope of this invention that other plants of the family of Orchidaceae plants which are of a genera having a pseudo bulb may be useful to obtain the extract of the present invention. For example, Orchidaceae plants having such a pseudo bulb are classified into the following genera:

Calypso Salish., Tipularia Nutt., Arundina Blume, Bletilla Reichb.fil., Liparis L. C. Richard, Eleorchis F. Maek., Malaxis Soland., Spathoglottis Blume, Acanthophippium Blume, Tainia Blume, Hancockia Rolfe, Geodorum Jackson, Eulophia R. Br., Cremastra Lindl., Kitigorchis F. Maek., Oreorchis Lindl., Cymbidium Sw., Eria Lindl., Bulbophyllum Thou.

As used herein, an extract of the present invention is a composition containing at least one active ingredient that is useful for promotion of hair growth that can be extracted from the above-mentioned plants of the present invention. As used herein, the term "active ingredient" refers to a component or mixture of components present in an extract of the present invention which has the property of promoting hair growth on an area of skin afflicted with alopecia. An extract of the present invention can be produced by an extraction process from a portion of a plant of the present invention. Such extraction processes are known in the art and embodiments of such processes are described herein. An extract of the present invention can also be produced by formulating a defined mixture of one or more active ingredients which have either been purified from the extract of the present invention or artificially produced by chemical methods.

The plants of the present invention can be cultivated plants (for example, from greenhouse cultivation or transplant cultivation) or grown in nature.

While the hair growth promoter of the present invention contains the aforementioned plant extract comprising at least one active ingredient, it is a preferred embodiment of the present invention to include one or more additional components in such a composition, such as those used in conventional hair tonics. Combining one or more of these components with the plant extract can produce a more effective hair growth promoter. Ingredients which can be combined with the extract of the present invention include vitamins, amino acids, animal oils, plant oils, sodium chloride, and mixtures thereof.

Vitamins useful in the composition of the present invention include, but are not limited to, Vitamin A, Vitamin $B_1$, Vitamin $B_2$, Niacin (nicotinic acid), Vitamin C, Vitamin E, sodium pantothenate, potassium pantothenate, and biotin H (Vitamin H). Vitamin A is useful for the health of the mucous membrane and nerves and has been shown to have an excellent effect against follicular keratoderma. Vitamin $B_1$, Vitamin $B_2$, and Niacin not only stabilize the nerves of skin and mucous membrane but also strengthen and protect (i.e. activate) the head (scalp) skin and are used in cellular respiration. Vitamin C promotes the metabolism of the skin cells of the scalp. Sodium pantothenate and potassium pantothenate improve the quality of the hair and prevent white hair. Vitamin E acts to facilitate the circulation of the blood or reactivate the hair matrix cells. Biotin H (vitamin H) in a mixture of a plant oil facilitates the activation of the hair root and prevents the hair from falling out.

A preferred amino acid to be used in a composition of the present invention is 2-amino-3-(3,4-dihydroxyphenyl) propanoic acid, which can also be referred to as Dopa. 2-amino-3-(3,4-dihydroxyphenyl)propanoic acid, is oxidized to a precursor of melanin by enzymatic action and is then degraded to melanin for the synthesis of new skin and hair cells.

Examples of animal and plant oils that can be used in the composition of the present invention include, but are not limited to, horse oil (refined from horse fats), egg oil (extracted from egg yolk), olive oil, camellia oil, rape seed oil, sesame oil, and germ oil. Animal and plant oils act to soften the skin of the scalp. In a preferred embodiment, sesame oil, when mixed with biotin H, activates the hair root and prevents the hair from falling out.

Sodium chloride facilitates the absorption of the extract of the present invention into the scalp through osmotic action by adjusting the concentration of sodium chloride added to the extract. This allows the individual components of the composition to permeate into the depth of the hair follicle to activate the hair root. As a result, the plant extract promotes the growth and strengthening of the hair and reduces hair loss within a short period of time.

The Calanthe R. Br. or Phaius Lour. plant extract of the present invention is an essential ingredient of the present composition which is useful in promoting hair growth. Preferably, other components of the hair growth composition, as described herein (i.e., vitamins, amino acids, etc.), are combined with the plant extract in order to enhance the effects of the composition; however, inclusion of such other components is not requisite to produce and use the hair growth promoter of the present invention.

In a preferred embodiment of the present invention, biotin H, sesame oil and sodium chloride are combined with the plant extract. In a more preferred embodiment, 2-amino-3-(3,4-dihydroxyphenyl)propanoic acid is further combined with the biotin H, sesame oil and sodium chloride, such as for use in cases where the hair has been lost entirely. Germ oil can also be combined with the above-mentioned ingredients to shorten the rehabilitation period of the hair.

In one embodiment, the preferable percentage by weight of 2-amino-3-(3,4-dihydroxyphenyl)propanoic acid in a composition of the present invention ranges from 0.05 to 1.0%, and more preferably from 0.1 to 0.3%. A preferred percentage by weight of biotin H in a composition of the present invention ranges from 0.05 to 0.5%, and more preferably from 0.1 to 0.5%. A preferred percentage by weight of sesame oil in a composition of the present invention ranges from 0.1 to 3.0%, and more preferably from 0.5 to 1.5%. A preferred percentage by weight of germ oil in a composition of the present invention ranges from 0.1 to 3.0% and more preferably from 0.5 to 1.5%. A preferred percentage by weight of sodium chloride in a composition of the present invention ranges from 0.5 to 5.0% and more preferably from 1.0 to 2.0%. It is appreciated that in the hair growth promoter comprising the plant extract of the present invention, the ratio of these components is not limited to the percentages listed herein. The percentages may be changed depending on the condition of an individual patient to synergistically promote the action of hair growth.

In another preferred embodiment of the present invention, a composition useful in promoting hair growth within a short period of time preferably comprises, in addition to the plant extract, biotin H, sodium pantothenate, niacin, sodium chloride, sesame oil, germ oil, and horse oil.

In another embodiment related to the hair growth promoter of the present invention, the composition contains at least biotin H, sesame oil and sodium chloride. In one embodiment, 100 to 200 ml of Orchidaceae plant extract as described herein is combined with 1,000 ml of a mixture of 0.1 to 0.15% biotin H by weight, 0.5 to 1.5% sesame oil by weight, and 1.0 to 2.0% sodium chloride by weight. In this embodiment, when the hair growth promoter is applied to a patient whose hair has fallen out or thinned out, the osmotic action of sodium chloride permits the sesame oil and biotin H to penetrate into the depth of the hair follicle to activate the hair root. The plant extract promotes the growth and strengthening of the hair and reduces hair loss within a short period of time.

In another embodiment of the present invention, the hair growth promoter composition comprises 2-amino-3-(3,4dihydroxyphenyl)propanoic acid, biotin H, sesame oil, and sodium chloride. Preferably, 100 to 200 ml of said plant extract is combined with 1,000 ml of a mixture of 0.1 to 0.3% 2-amino-3-(3,4-dihydroxyphenyl)propanoic acid by weight, 0.1 to 0.15% biotin H by weight, 0.5 to 1.5% sesame oil by weight, and 1.0 to 2.0% sodium chloride by weight. In this embodiment, when the hair growth promoter is applied to a patient whose hair has been lost entirely, 2-amino-3(3,4-dihydroxyphenyl)propanoic acid is degraded by enzymatic action in the body to produce melanin required for new skin and hair, and rehabilitates hair within a short period of time.

In yet another embodiment of the present invention, the hair growth promoter composition comprises 2-amino-3-(3, 4-dihydroxyphenyl)propanoic acid, biotin H, sesame oil, germ oil and sodium chloride. Preferably, 100 to 200 ml of said plant extract is combined with 1,000 ml of a mixture of 0.1 to 0.3% 2-amino-3-(3,4-dihydroxyphenyl)propanoic acid by weight, 0.1 to 0.15% biotin H by weight, 0.5 to 1.5% sesame oil by weight, 0.5 to 1.5% germ oil by weight, and 1.0 to 2.0% sodium chloride by weight. In this embodiment, the hair growth promoter displays superior results from the effect of the germ oil which softens the skin of the scalp, thereby further shortening the rehabilitation period of the hair.

It is within the scope of the present invention that a composition comprising the extract of the present invention can be used in conjunction with other known treatments for various types of alopecia in order to enhance the promotion of hair growth. For example, a composition of the present invention can be used with anti-inflammatory medicine to treat patients suffering from *alopecia areata*.

The composition of the present invention is useful for promoting hair growth when applied to an area of skin afflicted with alopecia. A composition of the present invention may also be referred to as a "hair growth promoter." Reference herein to promoting hair growth refers to increasing the growth of the hair above the amount of growth that would occur in the absence of the composition of the present invention. In one embodiment of the present invention, promotion of hair growth includes restoration of hair growth in an area of skin in which the hair has fallen out completely.

As used herein, the term "alopecia" refers to a condition that is identified by the unnatural absence of hair. An absence of hair can be partial or complete loss of hair from the scalp or body, or can refer to a thinning of the hair of the scalp or body. The composition of the present invention is useful for treating various types of alopecia. Preferably, such types of alopecia include *androgenic alopecia, alopecia areata*, or trauma-induced alopecia. The term "treating" can refer to preventing a type of alopecia, reversing a type of alopecia by restoring hair growth, or slowing the occurrence of a type of alopecia, e.g., by slowing the rate at which hair would otherwise be lost in the absence of a treatment.

As used herein, an area of skin afflicted with alopecia refers to any part of the skin which has the characteristic of unnatural hair loss that is associated with alopecia, such as the scalp.

A composition of the present invention is applied to the skin topically by any means of topical application known in the art. A composition of the present invention can be applied at a variety of time intervals, such as daily or weekly, depending on the individual patient. A composition of the present invention is preferably applied to skin that has been gently washed with a mild soap or shampoo, and then gently dried, for example, by towel blotting.

A composition of the present invention is applied in appropriate volumes such as can be readily determined by one of ordinary skill in the art. For example, a preferred volume of a composition of the present invention to be applied to a scalp afflicted with alopecia is about 2.5 ml.

One embodiment of the present invention relates to a process for producing an extract to be used as an active ingredient in a composition useful for promotion of hair growth. In such a process, a portion of a plant of genera Calanthe R. Br. or Phaius Lour., and preferably *Calanthe discolor* Lindl. or *Phaius flavus* (Blume) Lindl. is extracted. As used herein, "a portion of" a plant refers to any part of a plant, including the whole plant, the flower, the root, the stem, the leaf, or any mixture thereof. A preferred portion of the plant to use in the extraction process of the present invention is the pseudo bulb.

An extract of the present invention can be obtained by extraction of a portion of a plant of the present invention in an extraction solvent. It will also be appreciated that a useful composition of the present invention includes one or more active ingredients present in such an extract. Such an active ingredient can be purified and identified from an extract of the present invention by methods known in the art. For example, individual components of an extract of the present invention can be purified by standard fractionation techniques known in the art. Individual fractions can then be tested for the ability to promote hair growth, such as in the C3H mouse model as described herein. Once active ingredients are identified, a composition of the present invention can be produced by direct chemical synthesis of such active ingredients, purification of such active ingredients from an extract, or production of an extract of the present invention as described herein.

In one embodiment of an extraction process, the portion of plant to be extracted is washed with water after removing adhering matter such as mud from the plant. The plant is cut into small pieces using a knife or other cutting instrument. Preferably, a "small piece" of a plant is a 1 cm³ piece, but is not limited to this size. The plant pieces are immersed in an extraction solvent with or without stirring to form an extract liquid by heated reflux. The extracted liquid is filtered to remove solids and impurities. The impurities are reextracted in extraction solvent and filtered as described above. The filtered extracts are combined and can be used in this form or, alternatively, the extraction solvent is evaporated under reduced pressure, until the extract is reduced to a lyophilized form. The lyophilized extract can be stored and rehydrated as needed for preparation of a hair growth promoter of the present invention.

A preferred extraction solvent used to produce the extract of the present invention is an alcohol. A preferred alcohol to be used as an extraction solvent is ethanol or methanol. If methanol is used, all methanol must be evaporated from the resulting extract before such an extract can be used in a composition of the present invention. Such a solvent can be used in concentration from about 20% to about 100%. In a preferred embodiment of the present invention, the extract is drawn by using a hydrated alcohol as an extraction solvent. Most preferably, hydrated ethanol is used as an extraction solvent. Preferably, the solvent is an aqueous solution containing about 25% to about 100% of the alcohol by weight. More preferably, the solvent is an aqueous solution containing about 60% to about 80% alcohol by weight.

In a preferred embodiment of the process for producing an extract of the present invention, the pieces of plant are immersed in the extraction solvent for at least about 3 hours. In a more preferred embodiment, the pieces of plant are immersed in extraction solvent for at least about 10 days. In another preferred embodiment, the pieces of plant are immersed in extraction solvent for between about 1 month to about 2 months. Such an extraction is preferably performed in a cool, dark environment without stirring.

A lyophilized extract for use in a composition of the present invention is rehydrated in a solvent prior to formation of the composition. A preferred solvent for rehydration is a hydrated alcohol. As used herein, a hydrated alcohol is an aqueous alcohol solution that is a solution of an alcohol mixed with water. A more preferred solvent is hydrated ethanol. Most preferably, 75% hydrated ethanol is used to rehydrate an extract of the present invention. In a preferred embodiment, a lyophilized extract of the present invention is rehydrated in a solvent to form a solution that is about 2% to about 4% extract.

An extract of the present invention may also be used as directly extracted liquid, without lyophilization. In one embodiment, the hair growth promoter composition of the present invention is prepared by combining the obtained plant extract solution described above with benzoic acid as a preservative, vitamin E as an antioxidant, or vitamin C as a modifier of a pH which is appropriate for use in general cosmetics, or by diluting with water or alcohol, in order to increase its shelf life. The plant extract solution, when used directly without lyophilization, is preferably diluted to about 5% to about 40% in the total amount of solution, more preferably to about 10% to about 30% in the total amount of solution, and most preferably to about 10% to about 20% in the total amount of solution.

In more preferred embodiments of the present invention, other components such as vitamins, amino acids, animal oils, plant oils, sodium chloride, and mixtures thereof are added to the composition, as described heretofore.

The following examples are provided for the purposes of illustration and are not intended to limit the scope of the present invention.

EXAMPLES

The invention is illustrated in more detail by reference to the following examples:

Example 1

The following example illustrates the preparation of a hair growth promoter of the present invention.

3 gm of niacin, 3 gm of vitamin $B_1$, 3 gm of sodium pantothenate, 2 gm of potassium pantothenate, and 2 gm of benzoic acid are dissolved in 50 ml of warm water. 14 gm of vitamin C are dissolved in 330 ml of warm water. 1 gm of vitamin A is dissolved in 40 ml of ethanol; 7 gm of sesame oil are dissolved in 60 ml of ethanol; and 5 gm of vitamin E are dissolved in 25 ml of ethanol. 10 ml of 92% glycerol are added to 10 gm of horse oil and dissolved in 30 ml of ethanol. 30 ml of 92% glycerol are added to 1 gm of biotin H and dissolved by heating in 70 ml of ethanol and 50 ml of water. Further, 20 gm of sodium chloride are dissolved in 105 ml of water. The above solutions are mixed, to which 0.01 gm of vitamin $B_2$ is added to obtain a mixed solution 1.

300 gm cut pieces of pseudo bulb of *Calanthe discolor* Lindl. are immersed in 1,000 ml of 35% ethanol by weight and are extracted for at least about 10 days. The resulting extract is then filtered to remove impurities. 120 ml of the extract are added to solution 1 to obtain a hair growth promoter.

Example 2

The following example illustrates the preparation of a hair growth promoter of the present invention.

3 gm of niacin, 3 gm of vitamin $B_1$, 3 gm of sodium pantothenate, 2 gm of potassium pantothenate, and 2 gm of benzoic acid are dissolved in 50 ml of warm water. 14 gm of vitamin C are dissolved in 80 ml of warm water. And 1 gm of 2-amino-3-(3,4-dihydroxyphenyl)propanoic acid is dissolved in 250 ml of warm water. 1 gm of vitamin A is dissolved in 40 ml of ethanol; 7 gm of sesame oil are dissolved in 60 ml of ethanol; and 5 gm of vitamin E are dissolved in 25 ml of ethanol. 10 ml of 92% glycerol are added to 10 gm of horse oil and dissolved in 30 ml of ethanol. 30 ml of 92% glycerol are added to 1 gm of biotin H and dissolved by heating in 70 ml of ethanol and 50 ml of water. 20 gm of sodium chloride are dissolved in 105 ml of water. The above solutions are mixed, to which 0.01 gm of vitamin $B_2$ is added to obtain a mixed solution 2.

300 gm cut pieces of pseudo bulb of *Calanthe discolor* Lindl. are immersed in 1,000 ml of 35% ethanol by weight and extracted for at least about 10 days. The resulting extract is filtered to remove impurities. 120 ml of the extract are added to solution 2 above to obtain a hair growth promoter.

Example 3

The following example illustrates the preparation of a hair growth promoter of the present invention.

3 gm of niacin, 3 gm of vitamin $B_1$, 3 gm of sodium pantothenate, 2 gm of potassium pantothenate, and 2 gm of benzoic acid are dissolved in 50 ml of warm water. 14 gm of vitamin C are dissolved in 80 ml of warm water. 1 gm of 2-amino-3-(3,4-dihydroxyphenyl)propanoic acid is dissolved in 250 ml of warm water. 1 gm of vitamin A is dissolved in 40 ml of ethanol; 7 gm of sesame oil and 7 mg of germ oil are dissolved respectively in 30 ml of ethanol; and 5 gm of vitamin E are dissolved in 25 ml of ethanol. 10 ml of 92% glycerol are added to 10 gm of horse oil and dissolved in 30 ml of ethanol. 30 ml of 92% glycerol are added to 1 gm of biotin H and dissolved by heating in 70 ml of ethanol and 50 ml of water. 20 gm of sodium chloride are dissolved in 105 ml of water. The above solutions are mixed, to which 0.01 gm of vitamin $B_2$ is added to obtain a mixed solution 3.

300 gm cut pieces of pseudo bulb of *Calanthe discolor* Lindl. are immersed in 1,000 ml of 35% ethanol by weight and extracted for at least about 10 days. The resulting extract is then filtered to remove impurities. 120 ml of the extract are added to mixed solution 3 to obtain a hair growth promoter.

In the Examples 1, 2, and 3 described herein, the ratio of each ingredient to the gross weight is 0.1% by weight of 2-amino-3-(3,4-dihydroxyphenyl)propanoic acid, 0.1% by weight of biotin H, 0.7% by weight of sesame oil, 0.7% by weight of germ oil, or 2.0% weight of sodium chloride in the preparation of mixed solution 1, 2 or 3. It is noted that the mixed solution is not necessarily limited to this ratio, and experiments have shown that if the ratio is 0.1 to 0.3% by weight of 2-amino-3-(3,4-dihydroxyphenyl)propanoic acid, 0.1 to 0.15 % by weight of biotin H, 0.5 to 1.5% by weight of sesame oil, 0.5 to 1.5% by weight of germ oil, or 1.0 to 2.0% by sodium chloride, the anticipated effect is attained.

Furthermore, in the aforementioned examples, the amount of the plant extract that is combined with 1,000 ml of mixed solution 1, 2, or 3 is 120 ml, but the plant extract is not necessarily limited to this amount. Experiments have shown that if the amount of the plant extract to be combined with 1,000 ml of mixed solutions 1, 2 or 3 is between about 100 to about 200 ml, the anticipated effect is achieved.

Furthermore, in each of the Examples 1, 2, and 3, use of the extract of a pseudo bulb of *Calanthe discolor* Lindl. can promote the growth and strengthening of the hair by its action as described hereinafter, but an extract drawn from a pseudo bulb of *Phaius flavus* (Blume) Lindl. or a subterranean stem of *Oreorchis patens* Lindl. is also found to have similar action. Therefore, it is possible to use the pseudo bulb of *Phaius flavus* (Blume) Lindl. or the subterranean stem of *Oreorchis patens* Lindl. in place of *Calanthe discolor* Lindl. In this case, an extract from the pseudo bulb of *Phaius flavus* (Blume) Lindl. or the subterranean stem of *Oreorchis patens* Lindl. can be produced by the same process as for the pseudo bulb of *Calanthe discolor* Lindl.

Example 4

The following example illustrates the preparation of a Calanthe extract of the present invention.

Fresh pseudo bulb of *Calanthe discolor* Lindl. is washed and cut into small pieces. The pieces are immersed in 10 liters of 70% ethanol and the immersion is placed in a cool, dark room for 1 to 2 months, without stirring. The liquid extract is filtered to remove impurities and solids.

Example 5

The following example illustrates the preparation of a hair growth promoter of the present invention.

An extract is prepared from *Calanthe discolor* Lindl. as described in Example 4. 3–15 ml of the extract (preferably 8.8 ml) is added to a solution containing 10–50 mg of biotin (preferably 40 g), 1–3 g of sodium chloride (preferably 1.8 mg), and 3–20 mg of horse oil (preferably 20 mg). The following ingredients may then be added to the solution: 100–200 mg of nicotinamide (preferably 150 mg); 150–250 mg of sodium pantothenate (preferably 195 mg); and 1–3 g of ascorbic acid (preferably 1.85 g).

Example 6

As discussed in the background, the C3H mouse strain is a widely used model in the art for investigating hair growth mechanisms and for determining the effectiveness of promoters or inhibitors of hair growth. This example demonstrates the use of a hair growth composition of the present invention to promote hair growth in C3H/HeNCrj mice as compared to other compositions. Therefore, this example illustrates the pharmacological effectiveness of a hair growth composition of the present invention to promote hair growth.

C3H/HeNCrj mice, a C3H strain purchased from Charles River, Japan, were bred and housed in a facility maintaining high standards for pathogen control. The backs of 57 day old C3H/HeNCrj mice, were shaved using a hair clipper. The hair cycle of 57 day old C3H mice is in the second telogen phase (non-growth phase), as illustrated in FIG. 1. Beginning at 61 days of age, applications of the compositions listed in Table 1 were applied to the shaved area of each mouse, by placing the extract on the back with a pipet and spreading it evenly across the shaved area with a spatula. There were 8–10 mice in each group.

TABLE 1

| Sample number | Extract in composition |
| --- | --- |
| SS1 | Ginseng |
| SS2 | Bletilla |
| SS3 | Calanthe (leaves only) |
| SS4 | Calanthe (pseudo bulb) |

TABLE 1-continued

| Sample number | Extract in composition |
| --- | --- |
| SS5 | Sri Lanka poisonous plant |
| SS6 | Second Sri Lanka plant |
| SS7 | Calanthe (whole plant) |
| SS8 | Croton oil (positive control) |

A small-format, opaque digitizer, which uses a three-phase electromagnetic induction system to accurately measure a defined area (Graphtec KD Series, Model KD3220, Graphtec Corporation, Yokohama, Japan), was used to calculate the percent ratio of areas of hair regrowth against the entire shaved area. The hair regrowth measured in all cases was measurement of normal hair. Results are shown in FIG. 2.

Figure 2:
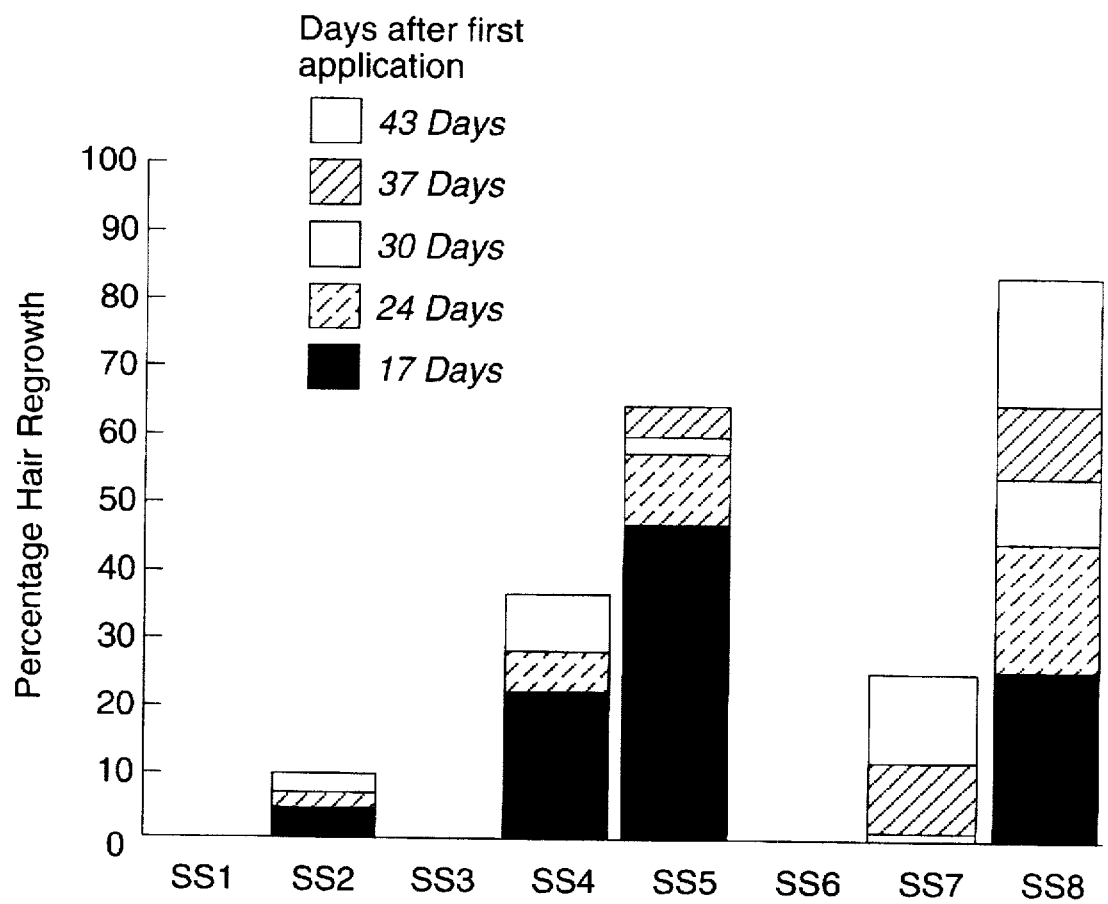
FIG. 2 shows percentages of hair regrowth in shaved C3H mice treated with various compositions, including extracts derived from *Calanthe discolor* Lindl.

FIG. 2 shows that the extracts of the present invention, from the Calanthe whole plant or pseudo bulb (SS4 and SS7), promote hair growth in comparison to other extracts used. Controls extracts from Ginseng, Bletilla, and Sri Lanka plants are included to serve as a point of comparison to demonstrate the effectiveness of the Calanthe extract. It is noted that the Calanthe extract of samples SS4 or SS7 showed significantly greater promotion of hair growth than an extract of an Orchidaceae plant of genus Bletilla, which has been disclosed as a hair growth promoter in the literature (See Yasunori et al., Japanese patent JP 1038012; Chiharu et al., Japanese patent JP 5155738; Kose et al., Japanese patent JP 5155738A). The Calanthe extract also showed significantly greater promotion of hair growth than an extract from Ginseng. Although SS5 and SS8 also showed promotion of hair growth, these extracts are either poisonous or carcinogenic, and therefore would not be useful in a composition of the present invention. These results clearly show the pharmacological effectiveness of a hair growth promoter of the present invention.

Example 7

The following example illustrates the use of a hair growth composition of the present invention to promote hair growth in C3H/HeNCrj mice, and demonstrates the pharmacological effectiveness of such a composition on hair growth.

a) Preparation of the extract: 2.2 kg of fresh pseudo bulb of *Calanthe discolor* Lindl. was washed and cut into small pieces. The pieces were immersed in 10 liters of 100% ethanol and extracted under heated reflux for three hours. The liquid extract was filtered to remove impurities and solids. The impurities were then reextracted and filtered as above. The combined liquid extract (about 30 liters) was evaporated under reduced pressure, and about 36.0 g of powdered extract was recovered.

b) Preparation of the test solution: 2.0 g or 4.0 g of powdered extract obtained above was dissolved in 75% ethanol to obtain 100 ml of either 2% or 4% (w/v) solution.

c) Testing of the extract on C3H mice: The C3H/HeNCrj mice were bred and housed so as to minimize exposure to potential pathogens. The backs of 57 day old male C3H/HeNCrj mice, weighing between 23 and 28 grams, were shaved using a hair clipper. The hair cycle of 57 day old C3H mice is in the second telogen phase (non-growth phase), as illustrated in FIG. 1. At 61 days of age, 0.1 ml of the above-prepared *Calanthe discolor* Lindl. extract was applied to the shaved area of each mouse, by placing the extract on the back with a pipet and spreading it evenly across the shaved area with a spatula. 10 mice received the 2% extract solution and 10 mice received the 4% extract solution. The extract was applied in similar manner for five consecutive days each week for 43 days after the first application. On days 18, 24, 30, 37 and 43 after the first application, the percentage ratio of the size of the area in which normal hair was regrowing against the size of the whole shaved area was determined. The size of these respective areas were determined by a Digitizer, as described in Example 6, which uses a three-phase electromagnetic induction system to accurately measure the indicated area. The mean hair growth and standard deviation for each group as calculated above is shown in FIG. 3.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A composition for increasing the rate of hair growth during anagen phase, comprising an effective amount of extract obtained from a plant having a pseudo bulb, wherein said plant is of a genera selected from the group consisting of Calanthe R. Br. and Phaius Lour.

2. The composition of claim 1, wherein said extract is obtained from a plant selected from the group consisting of *Calanthe discolor* Lindl. and *Phaius flavus* (Blume) Lindl.

3. The composition of claim 1, wherein said extract is obtained from a pseudo bulb of said plant.

4. The composition of claim 1, further comprising at least one component selected from the group consisting of vitamins, amino acids, animal oils, plant oils, sodium chloride, and mixtures thereof.

5. The composition of claim 1, wherein said extract is prepared by use of an aqueous solution containing between 25% to about 100% by weight of a hydrated alcohol as an extraction solvent.

6. The composition of claim 1, wherein said extract is prepared by use of an aqueous solution containing between about 60% to about 80% by weight of a hydrated alcohol as an extraction solvent.

7. The composition of claim 1, further comprising biotin H, sesame oil and sodium chloride.

8. The composition of claim 7, further comprising 2-amino-3-(3,4-dihydroxyphenyl)propanoic acid.

9. The composition of claim 9, further comprising germ oil.

10. The composition of claim 8, further comprising sodium pantothenate, potassium pantothenate, niacin, germ oil and animal oil.

11. A composition for increasing the rate of hair growth during anagen phase, comprising an effect amount of an extract of a plant of a genera selected from the group consisting of Calanthe R. Br. and Phaius Lour.; biotin H in an amount between about 0.05% to about 0.5% by weight; sesame oil in an amount between about 0.1% and about 3.0% by weight; and sodium chloride in an amount between about 0.5% and about 5.0% by weight.

12. The composition of claim 11, further comprising 2-amino-3-(3,4-dihydroxyphenyl)propanoic acid in an amount between about 0.05% to about 1.0% by weight.

13. The composition of claim 11, wherein said biotin H is present in an amount between about 0.1% and about 0.15% by weight; said sesame oil is present in amount between about 0.5% and about 1.15% by weight; said sodium chloride is present in an amount between about 1.0% and about 2.0% by weight; and said 2-amino-3-(3,4-dihydroxyphenyl) propanoic acid is present in an amount between about 0.1% and about 0.3% by weight.

14. A process for producing an extract useful as an active ingredient in a composition which is useful for increasing the rate of hair growth during anagen phase, comprising contacting a plant of a genera selected from the group consisting of Calanthe R. Br. and Phaius Lour. with an extraction solvent.

15. The process of claim 14, wherein said method comprises contacting a pseudo bulb of said plant with an extraction solvent.

16. The process of claim 14, wherein said extraction solvent is an aqueous solution comprising between about 25% and about 100% by weight of a hydrated alcohol.

17. The process of claim 14, further comprising the steps of:
   a) cleaning adhering matter from said plant;
   b) cutting said plant into pieces;
   c) immersing said pieces of said plant in the extraction solvent to form an extract liquid; and
   d) filtering the extract liquid to remove impurities.

18. The process of claim 17, wherein said step of immersing comprises immersing said pieces of said plant while stirring the resulting mixture for a time period of between about 1 month and about 2 months.

19. The process of claim 17, further comprising the step of combining said extract with at least one ingredient selected from the group consisting of vitamins, amino acids, animal oils, plant oils and sodium chloride.

20. A method for increasing the rate of hair growth during anagen phase, said method comprising the steps of applying an effective amount of a composition comprising an extract of a plant of a genera selected from the group consisting of Calanthe R. Br. and Phaius Lour. to a portion of an area of skin having hair.

21. The method of claim 20, wherein said composition further comprises at least one ingredient selected from the group consisting of vitamins, amino acids, animal oils, plant oils and sodium chloride.

22. The method of claim 20, wherein said composition further comprises biotin H, sesame oil and sodium chloride.

23. A composition having at least one active ingredient for increasing the rate of hair growth during anagen phase, wherein said active ingredient is present in an effective amount in an extract produced from a plant of a genera selected from the group consisting of Calanthe R. Br. and Phaius Lour.

24. A composition for increasing the rate of hair growth during anagen phase, comprising an effective amount of an extract obtained from *Oreorchis patens* Lindl.

25. A method for increasing the rate of hair growth during anagen phase, said method comprising the steps of applying an effective amount of a composition comprising an extract derived from *Oreorchis patens* Lindl. to a portion of an area of skin having hair.

* * * * *